United States Patent
Wigbers et al.

(10) Patent No.: US 9,000,218 B2
(45) Date of Patent: Apr. 7, 2015

(54) PROCESS FOR PREPARING SECONDARY AMINES IN THE LIQUID PHASE

(71) Applicants: Christof Wilhelm Wigbers, Mannheim (DE); Johann-Peter Melder, Boehl-Iggelheim (DE); Bernd Stein, Alsbach-Haehnlein (DE)

(72) Inventors: Christof Wilhelm Wigbers, Mannheim (DE); Johann-Peter Melder, Boehl-Iggelheim (DE); Bernd Stein, Alsbach-Haehnlein (DE)

(73) Assignee: BASF SE, Ludwigshafen (DE)

(*) Notice: Subject to any disclaimer, the term of this patent is extended or adjusted under 35 U.S.C. 154(b) by 129 days.

(21) Appl. No.: 13/737,158

(22) Filed: Jan. 9, 2013

(65) Prior Publication Data

US 2013/0178656 A1 Jul. 11, 2013

Related U.S. Application Data

(60) Provisional application No. 61/585,253, filed on Jan. 11, 2012.

(30) Foreign Application Priority Data

Jan. 11, 2012 (EP) .................................. 12150717

(51) Int. Cl.
*C07C 209/00* (2006.01)
*C07C 209/16* (2006.01)
*C07C 209/86* (2006.01)

(52) U.S. Cl.
CPC ............. *C07C 209/16* (2013.01); *C07C 209/86* (2013.01); *C07C 2101/14* (2013.01); *C07C 2103/74* (2013.01)

(58) Field of Classification Search
CPC ...................................................... C07C 209/16
USPC .................................................. 568/478, 479
See application file for complete search history.

(56) References Cited

U.S. PATENT DOCUMENTS

| 4,206,150 | A | * | 6/1980 | Slaugh | ........................... | 564/480 |
| 4,792,622 | A | * | 12/1988 | Yokota et al. | .................. | 564/398 |
| 5,254,736 | A | * | 10/1993 | Forquy | ........................... | 564/480 |

FOREIGN PATENT DOCUMENTS

| EP | 0 526 318 A1 | 2/1993 |
| JP | 2011-26214 A | 2/2011 |

OTHER PUBLICATIONS

U.S. Appl. No. 13/948,736, filed Jul. 23, 2013, Schelwies, et al.
International Search Report Issued Apr. 2, 2013 in PCT/EP2013/050077 filed Jan. 4, 2013 with English translation of category of cited documents.

* cited by examiner

*Primary Examiner* — Sudhakar Katakam
(74) *Attorney, Agent, or Firm* — Oblon, McClelland, Maier & Neustadt, L.L.P.

(57) ABSTRACT

The present application relates to a process for preparing secondary amines by aminating excess primary or secondary alcohols with primary amines in the liquid phase in the presence of copper-comprising catalysts.

16 Claims, No Drawings

PROCESS FOR PREPARING SECONDARY AMINES IN THE LIQUID PHASE

The present application incorporates the provisional U.S. application No. 61/585,253, filed on Jan. 11, 2012, by reference.

The present application relates to a process for preparing secondary amines by aminating excess primary or secondary alcohols with primary amines in the liquid phase in the presence of copper-comprising catalysts.

Secondary amines are important, industrially utilized substances. They serve, for example, as polymerization and curing catalysts for the production of polymer moldings based on epoxides and polyurethanes, as corrosion inhibitors and as starting materials for flocculants and detergents. In addition, secondary amines are used as intermediates in crop protection.

Preparation of secondary amines by amination of alcohols or aldehydes with primary amines in the liquid and gas phase, and of aldehydes with primary amines in the liquid phase, in the presence of hydrogen and hydrogenation catalysts is known.

JP 2011026214 describes the reaction of primary alcohols having $C_1$ to $C_3$-alkyl groups with tert-butylamine in the gas phase in the presence of copper-comprising catalysts to give N-alkyl-tert-butylamine. In this process, however, only moderate selectivities and yields are achieved. For instance, in the preparation of N-ethyl-tert-butylamine, a yield of only 77% and a selectivity of 80.6% are achieved at 250° C. in the presence of CuO/ZnO catalysts. In addition, this process works in the gas phase, which requires a higher energy demand and makes it less favorable to obtain secondary amines on the industrial scale.

U.S. Pat. No. 4,206,150 describes, as comparative examples 6 and 7, processes for preparing secondary amines in which 1-dodecanol is reacted with monomethylamine or dimethylamine at 200° C. and 375 psi over a copper catalyst supported on $Al_2O_3$ in the liquid phase, the copper content being 10% and 3.9% by weight respectively and the amine being used in a three-fold excess relative to the alcohol. Disadvantages of this process are firstly the high content of by-products (14.1% $C_{24}+C_{25}$ amines), and the low catalyst stability, since it leaches out after the amination. The teaching from U.S. Pat. No. 4,206,150 is therefore that, for the preparation of secondary amines proceeding from primary or secondary alcohols with amines in the liquid phase, the catalyst must comprise, as well as copper, also molybdenum and/or tungsten in the form of metals and/or oxides thereof, and the amine must be used in excess relative to the alcohol, in order that the catalyst does not leach out over a prolonged period and good yields are achieved. Moreover, the distillative purification of a secondary amine prepared according to U.S. Pat. No. 4,206,150 is not possible in a simple manner either, since the distillation results in the formation of homoazeotropes of amine and water which cannot be separated by distillation.

EP-B 257443 describes a process for preparing trialkylamines by reaction of primary alcohols with ammonia or a primary alkylamine in the liquid phase in the presence of copper catalysts with $Al_2O_3$ as a support at temperatures in the range from 230° C. to 235° C., in which only very small amounts of secondary amines (approx. 3%) form. EP 257443 also discloses that, in the case of use of primary amines with primary alcohols in excess, and of a copper catalyst as a hydrogenation catalyst, in the case of use of temperatures below 240° C., it is possible to preferentially prepare tertiary alkylamines. The fact that preferentially secondary amines can be prepared with high yield and selectivity within the temperature range of less than 210° C. is not disclosed in EP-B 257443.

EP 588156 describes the reaction of alkanols with alkylamines and hydrogen in the presence of copper chromite/alkaline earth metal chromite catalysts at 180 to 210° C. and 40 to 120 bar in the liquid phase. The molar amine/alkanol ratio is 1.5:1 to 50:1, and so this process always works with an excess of amine. A disadvantage of this process is the use of chromium-containing and hence toxic catalysts.

DE 364 1666 discloses that secondary amines can be prepared by reaction of alcohols with an excess of primary amines at 150 to 250° C. and only 1 to 6 bar. This requires copper/nickel catalysts which additionally comprise an element from the platinum group, especially Pt, Pd, Ru or Rh. Disadvantages are firstly the use of expensive hydrogenation metals such as platinum, and secondly the use of excess amine, since this complicates the subsequent distillative separation. In addition, the water of reaction has to be removed intermittently or continuously from the reaction mixture.

It was an object of the present invention to provide a selective process for preparing secondary amines in the liquid phase, in which there is firstly no need to use any toxic catalysts, a long service life of the catalyst is ensured, and secondly the secondary amine is obtained both in high yields and with high selectivities. A further object was that of providing a process in which a simple and efficient workup of the secondary amine prepared from the reaction output is possible.

This object is achieved by a process for preparing secondary amines of the formula I

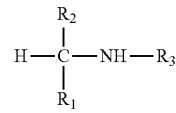

in which
$R_1$ and $R_2$ are each independently selected from the group of hydrogen, linear or branched aliphatic radicals having 1 to 15 carbon atoms, cycloaliphatic radicals having 5 to 10 carbon atoms, aralkyl radicals and phenyl radicals which may be o-, m- and/or p-substituted by aliphatic radicals having 1 to 4 carbon atoms, and
$R_3$ is selected from the group of linear or branched aliphatic radicals having 1 to 15 carbon atoms, cycloaliphatic radicals having 5 to 10 carbon atoms, aralkyl radicals and phenyl radicals which may be o-, m- and/or p-substituted by aliphatic radicals having 1 to 4 carbon atoms,
I) by aminating alcohols of the formula II

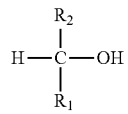

in which $R_1$ and $R_2$ are each as defined above
II) with primary amines of the formula III $$R_3-NH_2 \qquad III$$

in which $R_3$ is as defined above
III) and hydrogen in the liquid phase in the presence of hydrogenation catalysts, comprising the following steps:
(i) feeding alcohols of the formula II, primary amines of the formula III, hydrogen and optionally solvent into the hydrogenation reactor, the molar ratio of alcohol II to primary amine III being 1 to 20:1, (ii) performing the hydrogenation at temperatures of 150 to 210° C. and pressures of 1 to 300 bar in the presence of a hydrogenation catalyst comprising copper on oxidic supports.

Preference is given to the process according to the invention excluding secondary amines of the formula I which are prepared from 1-dodecanol as the compound of the formula II with monomethylamine as the compound of the formula III.

Preference is given to the process according to the invention when $R_1$, $R_2$ and $R_3$ are each selected from the group of linear or branched aliphatic radicals having 1 to 4 carbon atoms.

Preference is given to the process according to the invention when the catalyst precursor comprising copper oxides comprises 1 to 80% by weight of copper oxide.

Preference is given to the process according to the invention when the catalyst support used comprises aluminum oxides, silicon dioxide, titanium dioxides, zirconium dioxide, lanthanum oxide, molybdenum oxide, tungsten oxide or mixtures of these oxides.

Preference is given to the process according to the invention when it excludes hydrogenation catalysts which, as well as copper, also comprise tungsten and/or molybdenum as a metal and/or in the form of the oxides thereof.

Preference is given to the process according to the invention when the catalyst support used is aluminum oxide and/or lanthanum oxide.

Preference is given to the process according to the invention when the molar ratio of alcohol II to primary amine III is 1.5 to 15:1.

The process according to the invention, wherein the hydrogenation output after step (ii) is subjected to the following workup steps:
(a) distillatively removing alcohol II, optionally amine of the formula III and a portion of the water from the hydrogenation output,
(b) extracting the hydrogenation output which has been obtained from (a) and freed of alcohol II, optionally amine of the formula III and a portion of the water with an aqueous alkali metal and/or alkaline earth metal hydroxide solution,
(c) removing the aqueous phase obtained from step (b) from the organic phase,
(d) fractionally distilling the organic phase obtained from step c) to obtain secondary amine I and
(e) recycling optionally water-comprising alcohol II and/or amine of the formula III into hydrogenation step (ii).

Preference is given to the process according to the invention when the secondary amine of the formula I is N-ethyl-tert-butylamine.

The inventive reaction of ethanol with tert-butylamine and hydrogen to give ethyl-tert-butylamine can be described by the following formula equation:

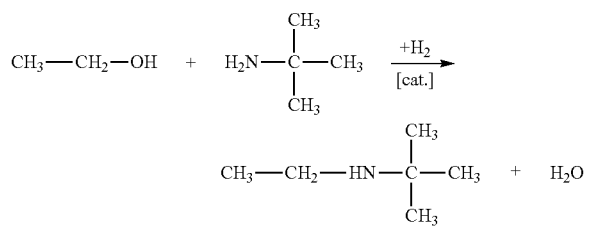

The amination is performed batchwise or continuously in the liquid phase. Preference is given to a continuous process.

To prepare the amines of the formula I, hydrogen, alcohols of the formula II and amines of the formula III are introduced into a hydrogenation reactor, optionally with a solvent.

The $R_1$ and $R_2$ radicals in the compounds of the formulae I and II in the process according to the invention are selected from the group of hydrogen, linear or branched aliphatic radicals having one to 15 carbon atoms, cycloaliphatic radicals having 5 to 10 carbon atoms, aralkyl radicals and phenyl radicals which may be o-, m- and/or p-substituted by aliphatic radicals having one to 4 carbon atoms. The aralkyl or phenyl radicals are preferably substituted by aliphatic radicals selected from the group of methyl, ethyl, n-propyl, i-propyl-, n-butyl-, i-butyl, sec-butyl and/or tert-butyl groups.

$R_3$ in the compounds of the formulae I and III is preferably selected from the group of linear or branched aliphatic radicals having one to 15 carbon atoms, cycloaliphatic radicals having 5 to 10 carbon atoms, aralkyl radicals and phenyl radicals which may be o-, m- and/or p-substituted by aliphatic radicals having one to 4 carbon atoms. The aralkyl or phenyl radicals are preferably substituted by aliphatic radicals selected from the group of methyl, ethyl, n-propyl, i-propyl, n-butyl, i-butyl, sec-butyl and/or tert-butyl groups.

Preferred primary alcohols of the formula II are selected from the group of methanol, ethanol, n-propanol, n-butanol, 2-methyl-1-propanol, pivalyl alcohol, n-pentanol, n-hexanol, 2-ethylhexanol, 2-methyl-1-pentanol, 3-methyl-1-pentanol, 4-methyl-1-pentanol, n-octanol, n-decanol, n-undecanol, n-dodecanol, 2-phenylethanol, 2-cyclopentylethanol, 2-cyclohexyl-ethanol, 2-cycloheptylethanol, methylphenylethanol, benzyl alcohol, methylbenzyl alcohol and mixtures of these alcohols.

Particularly preferred primary alcohols of the formula II are selected from the group of methanol, ethanol, n-propanol, n-butanol, 2-methyl-1-propanol and mixtures of these compounds.

Very particular preference is given to primary alcohols of the formula II selected from the group of methanol, ethanol, n-propanol, n-butanol and mixtures of these alcohols. Very especially preferred is ethanol.

Preferred secondary alcohols of the formula II are isopropyl alcohol, 2-butanol, cyclopentanol and cyclohexanol.

Particularly preferred secondary alcohols of the formula II are isopropanol and cyclohexanol.

Preferred amines of the formula III are methylamine, ethylamine, n-propylamine, i-propylamine, n-butylamine, 2-methyl-1-propylamine, 2-butylamine, tert-butylamine, n-hexylamine, n-decylamine, aniline, adamantylamine, dodecylamine, benzylamine. Particularly preferred amines of the formula III are tert-butylamine and adamantylamine.

More preferably, the secondary amine of the formula I which is prepared by reaction of 1-dodecanol as the alcohol of the formula II with methylamine as the amine of the formula III by the process according to the invention is excluded.

The amination of the alcohols of the formula II is performed in accordance with the invention at temperatures of 150 to 210° C., preferably 160 to 200° C. and more preferably 170 to 200° C.

According to the stoichiometry of the amination, no hydrogen is required proceeding from alcohols. It is advantageous, however, when hydrogen is supplied.

The total pressure in the reactor at the particular temperature is composed of the partial pressures of the feedstocks and of the reaction products, i.e. hydrogen, alcohol of the formula II, amine of the formula III, secondary amine I, water, and any solvent additionally used. Injection of hydrogen increases the pressure to the desired reaction pressure. In order to compensate for the consumption of hydrogen, the total pressure is kept constant over the reaction time by injecting further hydrogen.

The total pressure is 1 to 300 bar, preferably 20 to 250 bar, more preferably 25 to 250 bar and most preferably 30 to 150 bar.

The molar ratio of alcohol of the formula II to primary amine of the formula III is 1 to 20:1, preferably 1.5 to 15:1, more preferably 2 to 10:1 and most preferably 3 to 5:1. The selection of this molar ratio achieves a high selectivity of secondary amine I.

It may be advantageous to perform the process according to the invention in the presence of a solvent which is inert under the reaction conditions. These inert solvents are selected from the group of N-methylpyrrolidone and ethers such as tetrahydrofuran, dioxane, ethylene glycol dimethyl ether, and hydrocarbons such as toluene, o-, m-, p-xylene, and mixtures of these solvents.

However, it is preferable to work in the absence of a solvent.

The catalyst space velocity is generally in the range from 0.01 to 2 kg, preferably 0.05 to 1 kg and more preferably 0.1 to 0.5 kg of primary amine of the formula III per liter of catalyst (bulk volume) and hour.

For the process according to the invention using alcohols of the formula II and primary amines of the formula III, preference is given to catalyst precursors comprising copper oxides, the copper oxide being applied to oxidic supports. The amount of copper oxide, calculated as CuO, is 1 to 80% by weight, preferably 10 to 70% by weight and more preferably 20 to 65% by weight, based on the total mass of the oxidic catalyst precursor. This catalyst precursor is hydrogenated to give elemental copper either prior to the hydrogenation or in the initial phase of the hydrogenation in the presence of alcohols II and primary amines III. Suitable catalyst supports are, for example, aluminum oxide, silicon dioxide, titanium dioxide, zirconium dioxide, lanthanum oxide, tungsten oxide, molybdenum oxide and/or activated carbon. A catalytically active composition in this context is understood to mean the sum of oxygen-comprising copper compounds and oxidic supports.

Particularly preferred catalyst precursors comprising copper oxide on aluminum oxide can be prepared according to DE 3027890, examples 1 a and 2 a. The shaped bodies have a specific surface area of 50 to 120 m² per gram, and comprise entirely or partly crystals with spinel structure and copper in the form of copper oxide. These catalyst precursors are obtained by precipitating copper and aluminum in a ratio of 0.25 to 3 atoms of copper to one atom of aluminum from the compounds thereof in the presence of carbonates at a pH of 4.5 to 9, and calcining the precipitate thus obtained at a temperature of 300 to 800° C.

Likewise particularly preferred copper oxide on oxidic materials comprising aluminum oxide and at least one of the oxides of lanthanum, of tungsten, of molybdenum, of titanium or of zirconium are prepared according to WO 2004/085356 A 1, example 1. The oxidic material is admixed with pulverulent, metallic copper, copper flakes, pulverulent cement, graphite or a mixture thereof. Mixtures of these components are shaped to give a shaped body. The oxidic material comprises 50 to 80% by weight and preferably 55 to 75% by weight of copper oxide, 15 to 35% by weight and preferably 20 to 30% by weight of aluminum oxide and at least one of the oxides of lanthanum, of tungsten, of molybdenum, of titanium or of zirconium in an amount of 2 to 20% and preferably 3 to 15% by weight.

The catalytically active composition of the catalysts used in the process according to the invention may further comprise one or more elements in the 0 oxidation state or the inorganic or organic compounds thereof, selected from groups I A to VI A and I B to VII B and VIII of the Periodic Table of the Elements.

The preparation of supported copper catalysts is described in detail in applications DE 3027890 A 1 and WO 2004/085356 A 1. The content of these applications is fully incorporated into the present application.

The reactors used are preferably tubular reactors, the process according to the invention being performable in fresh gas mode or cycle gas mode. However, it is preferably performed in cycle gas mode. "Cycle gas mode" is understood to mean that unconverted hydrogen is not discharged from the process, but recycled into the hydrogenation reactor together with compounds which are gaseous under the reaction conditions of the hydrogenation output condensation. However, it is also possible to use excess hydrogen in another way or to burn it.

The oxidic catalyst precursors are ground, mixed with shaping assistants, shaped to tablets, balls, rings or extrudates, and reduced with hydrogen either outside or within the reactor and arranged in a fixed bed in the reactor.

The reactants in liquid form are passed continuously in liquid phase mode or trickle mode over the catalyst present in the reactor.

It is also possible to perform the process according to the invention in a fluidized bed with catalyst material in upward and downward fluidized motion.

It is advantageous to work up the hydrogenation output in accordance with the invention. The liquid hydrogenation output obtained after cooling and decompression comprises, as well as the target product, the secondary amine of the formula I, as by-products, small amounts of tertiary amine of the formula IV

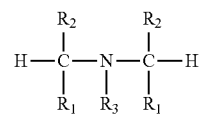

and also excess alcohol of the formula II, with or without small amounts of primary amine of the formula III. Small amounts are understood in each case to mean less than 10% by weight, preferably less than 5% by weight and more preferably less than 1% by weight of the compounds specified in each case. The amination forms about 5 to 20% by weight of water, based on the amount of the catalyst-free hydrogenation output. Secondary amines of the formula I, primary amines of the formula III and alcohols of the formula II can form azeotropes with water. It is therefore possible by distillation to remove only mixtures comprising water of reaction, amine of the formula I, amine of the formula III and/or alcohol of the formula II from the hydrogenation output.

EP-B 1312599 and EP-B 1312600 describe the separation of amine-containing mixtures comprising one or more amines, water, low boilers and high boilers. The separation is effected by
(i) separating off by distillation low boilers from the amine-containing mixture,
(ii) optionally separating off by distillation high boilers from the amine-containing mixture, (iii) extracting the amine-containing mixture with sodium hydroxide solution, producing an aqueous, sodium hydroxide-containing first phase and an aqueous-organic, amine-containing second phase, (iv) distilling the aqueous-organic second phase, producing an amine/water azeotrope and an essentially anhydrous amine, and recycling the amine/water azeotrope to the extraction step (iii).

The essentially anhydrous amine can, if required, be purified further by distillation. In one working example, the component steps of the workup are demonstrated on a hydrogenation output which has been obtained by reductive amination of 1,5-pentanediol with ammonia to form piperidine.

Preferably, for the process according to the invention, a workup of the hydrogenation output is likewise effected, which comprises both distillations and the breaking of amine/water or alcohol/water azeotropes with aqueous alkali metal and/or alkaline earth metal hydroxide solutions. Both the distillations and the breaking of the azeotropes can be performed batchwise or continuously.

In contrast to the teaching of EP-B 1312599 and EP-B 1312600, in the process according to the invention, excess alcohol, water of reaction and any unconverted amine of the formula III are first removed by distillation from the remaining reaction output. According to the structure of the alcohol, alcohol and water can be removed separately or as a separable mixture, as a homoazeotrope or as a heteroazeotrope.

Since methanol and water do not form an azeotrope, methanol can be removed separately or together with the water. If the removal is effected together, methanol and water can subsequently be separated in a further column. The methanol can be recycled into the amination.

Since ethanol, for example, forms a homoazeotrope with water, a mixture of ethanol and water is distilled off (at standard pressure 95.6% by weight of ethanol and 4.4% by weight of water). Since the water content of the azeotrope is low, it can be recycled into the inventive amination without removing the residual water.

Relatively long-chain alcohols of the formula II, for example butanols, form heteroazeotropes with water, i.e. have a miscibility gap. By phase separation, the alcohol can be separated from the water and recycled into the amination.

In the inventive amination, one mol of water forms according to the reaction equation. Therefore, distillation fractions which comprise water, alcohols of the formula II and/or primary amines of the formula III can be recycled into the synthesis stage (ii) of the process according to the invention.

If not all of the water of reaction has been removed from the hydrogenation output together with the alcohols II, there is azeotrope formation between secondary amine and water in the further distillative workup.

The residual water has to be removed from the hydrogenation outputs which have been freed of alcohol II and only a portion of the water of reaction. This is done by treating the hydrogenation output with aqueous alkali metal hydroxide and/or alkaline earth metal hydroxide solution. The alkali metal hydroxide and/or alkaline earth metal hydroxide concentration in the aqueous solution may be 1 to 75% by weight and preferably 25 to 50% by weight. Preferred aqueous alkali metal hydroxide and/or alkaline earth metal hydroxide solutions are selected from the group of sodium hydroxide solution, potassium hydroxide solution, magnesium hydroxide, calcium hydroxide. Preference is given to sodium hydroxide solution. Particular preference is given to a 50% by weight sodium hydroxide solution.

After extraction of the hydrogenation output with the aqueous alkali metal hydroxide and/or alkaline earth metal hydroxide solution, the latter is removed by phase separation. The residual water content of the organic phase can be determined, for example, by Karl Fischer titration. The amount of alkali metal hydroxide and/or alkaline earth metal hydroxide solution required for the water removal can be determined by a few preliminary tests.

The extraction apparatus used for the extraction with alkali metal hydroxide and/or alkaline earth metal hydroxide solution may have a one-stage or multistage configuration, for example a single mixer-settler extractor. Multistage extractions are, for example, extraction columns or extraction cascades. Suitable extraction columns are, for example, columns with random packing, sieve tray columns, cascade columns, pulsed columns, rotary columns and centrifugal columns. An extraction cascade is, for example, several mixer-settler-extractors connected in series, which may also be configured in a space-saving manner as a tower extractor or box extractor. If the extractor has two or more stages, preference is given to a countercurrent extraction column having generally 1 to 25 and preferably 4 to 10 theoretical plates. The latter is generally operated at a pressure at which all components of the extraction mixture are present below their boiling point, and also a viscosity of the two phases at which dispersion of the two phases is possible without any problem is established. The temperature is generally 5 to 200° C., preferably 20 to 70° C., and more preferably 40 to 50° C. After phase separation, the phase comprising aqueous alkali metal hydroxide and/or alkaline earth metal hydroxide solution is discharged from the process.

If the aqueous alkali metal hydroxide and/or alkaline earth metal hydroxide solution removed comprises significant amounts of secondary amine of the formula I, alcohol of the formula II and/or primary amine of the formula III, these compounds can be recovered by extraction with organic solvents. Significant amounts are present when the sum of the above compounds is more than 10% by weight, preferably more than 5% by weight and more preferably more than 2% by weight, based on the water- and catalyst-free hydrogenation output.

Useful organic solvents include, for example, aliphatic, cycloaliphatic or aromatic hydrocarbons which have a miscibility gap with aqueous alkali metal hydroxide and/or alkaline earth metal hydroxide solution. Examples of such hydrocarbons are n-hexane, n-octane, cyclohexane, toluene and ethylbenzene, or mixtures of these compounds.

The aqueous alkali metal hydroxide and/or alkaline earth metal hydroxide solution phase is removed from the hydrocarbon phase by phase separation. The hydrocarbon is removed by distillation from the hydrocarbon phase. The secondary amine of the formula I recovered, the alcohol of the formula II and/or the primary amine of the formula III can be combined with the majority of crude secondary amine of the formula I which has been obtained from the first organic phase after phase removal by extraction, and purified by distillation.

It is additionally possible to break any azeotrope of secondary amine of the formula I and water which forms by adding hydrocarbons to the hydrogenation output, distilling hydrocarbon/water heteroazeotropes out of the hydrogenation output, removing the water phase from the hydrocarbon phase, and recycling the hydrocarbon phase into the distillation.

The anhydrous hydrogenation output, or that comprising only less than 5%, preferably less than 3% and more preferably less than 1% by weight of water, can be purified further by fractional distillation. The distillation can, depending on the amounts to be distilled, be performed continuously or batchwise. First of all, if present, unconverted primary amine III distills overhead. This is followed by the amine of the formula I, which is likewise distilled overhead. Remaining in the bottoms are, if present, tertiary amines of the formula IV and high boilers. Fractions which comprise, according to GC analysis, less than 97 area %, more preferably less than 98 area % and more preferably less than 99 area % of secondary amine I can, if a purity of more than 97 area % is desired, be recycled into the distillation.

Useful apparatus for the fractional distillation is customary apparatus, as described, for example, in Kirk-Othmer, Encyclopedia of Chemical Technology, 3rd edition, volume 7, John Wiley and Sons, New York, 1979, pages 870 to 881. Preference is given to sieve tray columns, bubble-cap tray columns, columns with structured packing or columns with random packing.

Fractional distillation achieve purities of the secondary amines of the formula I of more than 98 area %, especially more than 99 area %, more preferably of more than 99.5 area % and especially of more than 99.9 (GC analysis).

For the continuous workup according to the disclosure of EP-B 1312599 and EP-B 1312600, three to four tailored distillation columns and one extraction apparatus are required.

In the case of the inventive batchwise workup, in contrast, only one to two distillation columns and one extraction apparatus are used.

EXAMPLES

General method for the amination of primary and secondary alcohols with primary amines in the liquid phase.

Catalyst Preparation

The copper catalyst precursor was prepared according to DE 3027890, example 1a. It had the composition of 55% by weight of CuO and 45% by weight of gamma-$Al_2O_3$, in the form of 3 ×3 mm tablets. The copper catalyst precursor was reduced with hydrogen according to example 1 b and passivated with air below 50° C. (catalyst A). A further copper catalyst precursor is effected according to WO-A1 04/085356, example 1 (catalyst B).

Experimental Procedure (Batchwise Mode)

The amination was conducted in a magnet-coupled 300 ml stirred autoclave with electrical heating and cascade control of internal temperature. The nitrogen-inertized autoclave was charged with the respective amounts of primary or secondary alcohol, primary amine and copper catalyst in reduced and passivated form. At room temperature, hydrogen was injected over the reaction mixture up to a pressure of 10 bar. Then the reaction mixture was heated to the envisaged reaction temperature, hydrogen was replenished up to the envisaged total pressure and stirring was effected under these conditions for the envisaged reaction time. The stirrer speed was 700 rpm.

After the envisaged reaction time, the reaction mixture was cooled and decompressed. The yield of the target products, the secondary amines I, the unconverted primary amines III and the tertiary amines as by-products were determined by gas chromatography (30 m RTX 5 amine column). The yield figures are GC area percentages. The secondary amine selectivity (S) is defined as area $\%_{sec.\ amine}$: (100–area $\%_{prim.\ amine}$)*100.

Examples 1 to 5

Amination of Ethanol with Tert-Butylamine to give Ethyl-Tert-Butylamine (Batchwise Mode)

Table 1 comprises the amounts of starting compounds and the reaction conditions. In all experiments, 10 g of copper catalyst A were used.

After two, six and 10 hours of reaction time, samples were taken and analyzed by gas chromatography for tert-butylamine, ethyl-tert-butylamine and diethyl-tert-butylamine.

Table 1 shows that, between 160 and 180° C., at tert-butylamine/ethanol molar ratios between 1:5 to 1:20, yields of ethyl-tert-butylamine between about 88 and 91% and selectivities up to 97% are achieved.

Particular emphasis is given to experiment 3, in which, after six hours of reaction time, 88.4 area % of ethyl-tert-butylamine and only 1.6 area % of diethyl-tert-butylamine were obtained. The uncoverted tert-butylamine (8.7 area %) can be removed by distillation and recycled into the synthesis. The selectivity is 96.8% (table 1).

Example 6

Amination of I-Propanol with Adamantylamine to give I-Propyladamantylamine (Batchwise Mode)

A mixture of 6 g of adamantylamine, 96 g of i-propanol, 15.4 g of o-xylene and 8 g of ground, reduced and passivated catalyst A were stirred in an inertized magnet-coupled 300 ml autoclave. Then 5 bar of hydrogen were injected. The mixture was heated to 200° C. The pressure rose to 29 bar. Hydrogen was replenished up to a total pressure of 40 bar. This was followed by stirring at 200° C. and total pressure 40 bar for 6 hours. Every two hours, samples were taken and analyzed by gas chromatography.

Table 2 shows that i-propyladamantylamine yields between 90 and 92% were achieved.

Example 7

Continuous Amination of Ethanol with Tert-butylamine to give Ethyl-Tert-Butylamine The hydrogenation was conducted for 241 hours in a tubular reactor (length 2500 mm, diameter 30 mm) which had been charged with 700 ml of the catalyst precursor (55% by weight of CuO, 45% by weight of $Al_2O_3$, 3×3 mm tablets) under nitrogen. The catalyst precursor was prepared according to DE 3027890 A 1, example 1 a.

The catalyst precursor was reduced under ambient pressure, first at 180° C. for 6 hours, then at 200° C. for 6 hours with mixtures of 20 l (STP) of hydrogen and 400 l (STP) of nitrogen, then at 200° C. for 6 hours with mixtures of 40 l (STP) of hydrogen and 400 l (STP) of nitrogen, and finally, after switching to pure hydrogen within 6 hours, with 200 l (STP) of hydrogen for 6 hours.

The hydrogenation was conducted in liquid phase mode at temperatures of 170 to 185° C., pressures of 50 bar and molar ratios of tert-butylamine to ethanol of 1:3 to 1:5. The catalyst space velocity was 0.15 to 0.30 kg per liter of catalyst and hour.

After 228 hours, according to GC analysis, the following result was achieved (yield=GC area %, ethanol was excluded from the GC analysis):

|  | Area % | |
| --- | --- | --- |
|  | after 109 h | after 228 h |
| Ethyl-tert-butylamine | 84.2 | 85.3 |
| Diethyl-tert-butylamine | 2.5 | 2.1 |
| tert-Butylamine | 13.0 | 12.5 |

Since tert-butylamine can be recovered in the workup, the ethyl-tert-butylamine selectivity is 97.5% after 109 hours, and 96.8% after 228 hours.

The reaction conditions after 109 and 228 hours of hydrogenation time were 170° C. and 50 bar. The molar ratio of tert-butylamine to ethanol was 1:3 (after 109-121 hours 1:10), the catalyst space velocity 0.25 g per liter of catalyst and hour.

The experiment shows that, in contrast to U.S. Pat. No. 4,206,150, comparative example 6, no deactivation of the copper catalyst is observed.

Examples 8 and 9

Amination of Ethanol or I-Propanol with Cyclohexylamine

The amination was conducted with ethanol or i-propanol and cyclohexylamine in the presence of 5 g of ground, reduced and passivated catalyst A according to the general method. The amounts of feedstock and reaction conditions are shown in table 3.

The GC analysis shows that a high selectivity for the desired secondary amines has been achieved. For instance, the GC areas of ethylcyclohexylamine and i-propylcyclohexylamine relative to the sum of the areas of secondary+tertiary amine are 94% and 99% respectively.

Unconverted cyclohexylamine and unconverted alcohols can be removed from the hydrogenation output and recycled into the synthesis stage.

TABLE 1

Preparation of ethyl-tert-butylamine (ETBA)

| Experiment No. | Ethanol [g] | tert-butyl-amine [g] | Molar ratio of amine to alcohol | Temperature [° C.] | Total pressure [bar] | GC area % 2 hours | | | | GC area % 6 hours | | | | GC area % 10 hours | | | |
|---|---|---|---|---|---|---|---|---|---|---|---|---|---|---|---|---|---|
| | | | | | | prim.[1] | sec.[2] | tert.[3] | S[4] | prim. | sec. | tert. | S[4] | prim. | sec. | tert. | S[4] |
| 1 | 92 | 7.3 | 1:20 | 160 | 80 | 36.3 | 57.9 | 0.2 | 90.9 | 0.7 | 89.6 | 6.3 | 90.3 | 0.1 | 78.5 | 17.6 | 78.1 |
| 2 | | 14.6 | 1:10 | | | 60.8 | 37.2 | 0 | 94.9 | 15.4 | 82.1 | 1 | 97.0 | 0.4 | 91.3 | 6.7 | 91.9 |
| 3 | | 29.2 | 1:5 | 170 | | 57.4 | 40.3 | 0.03 | 94.6 | 8.7 | 88.4 | 1.6 | 96.8 | 0.7 | 89.1 | 8.9 | 89.7 |
| 4 | | 7.3 | 1:20 | 180 | | 0.5 | 87.7 | 8.6 | 88.1 | 0.2 | 60.1 | 34.6 | 60.2 | 0.1 | 40.3 | 52.8 | 40.3 |
| 5 | | | | 210 | | 0 | 31.6 | 53.9 | 31.6 | 0 | 25.9 | 53.2 | 25.9 | 0 | 23.0 | 50.1 | 23.0 |

[1] tert-butylamine
[2] ethyl-tert-butylamine
[3] diethyl-tert-butylamine
[4] ETBA selectivity [%]

TABLE 2

Preparation of i-propyladamantylamine

| Experiment No. | Reaction time [h] | GC area % | | |
|---|---|---|---|---|
| | | adamantylamine | i-propyl-adamantylamine | di-i-propyl-adamantylamine |
| 6 | 2 | 9.8 | 90.2 | — |
| | 4 | 6.4 | 91.3 | — |
| | 6 | 6.7 | 90.7 | — |

TABLE 3

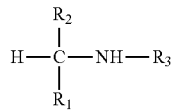

| Experiment No. | ROH R | ROH [g] | Cyclohexyl-amine [g] | Molar ratio of amine:ROH | T [° C.] | Total pressure | Reaction time | GC area % | | | | |
|---|---|---|---|---|---|---|---|---|---|---|---|---|
| | | | | | | | | prim[1] | sec[2] | tert[3] | ROH | N[4] |
| 8 | $C_2H_5$ | 100 | 43 | 1:5 | 170 | 80 | 6 | 13.1 | 34.8 | 2.1 | 45.2 | 4.8 |
| 9 | $i\text{-}C_3H_7$ | 105 | 35 | | | | | 0.9 | 42.0 | 0.2 | 50.0 | 6.9 |

[1] cyclohexylamine
[2] alkylcyclohexylamine
[3] dialkylcyclohexylamine
[4] N = sum of the secondary components

The invention claimed is:

1. A process for preparing a secondary amine of formula I:

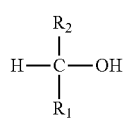

wherein
$R_1$ and $R_2$ are each independently hydrogen, a linear or branched aliphatic group having 1 to 15 carbon atoms, a cycloaliphatic group having 5 to 10 carbon atoms, a aralkyl group and a phenyl group optionally o-, m- and/or p-substituted by one or more aliphatic groups having 1 to 4 carbon atoms, and
$R_3$ is a linear or branched aliphatic group having 1 to 15 carbon atoms, a cycloaliphatic group having 5 to 10 carbon atoms, an aralkyl group and a phenyl group optionally o-, m- and/or p-substituted substituted by one or more aliphatic groups having 1 to 4 carbon atoms,
the process comprising:
charging an alcohol of formula II, a primary amine of formula III, hydrogen, a hydrogenation catalyst and optionally, a solvent to a hydrogenation reactor;
aminating the alcohol of formula II

II

with the primary amine of formula III and hydrogen in a liquid phase in the presence of the hydrogenation catalyst to obtain a reaction mixture comprising the secondary amine of formula I:

$R_3$—$NH_2$   III wherein
$R_1$, $R_2$ and $R_3$ are defined above,
a molar ration of the alcohol of formula II to the primary amine of formula III is from greater than 1:1 to 20:1,
a temperature of the amination is from 150 to 210° C.,
a pressure of the amination is from 1 to 300 bar, and
the hydrogenation catalyst comprises copper on an oxidic support.

2. The process according to claim 1,
wherein the compound of the formula II is not 1-dodecanol, and
and the compound of the formula III is not monomethylamine.

3. The process according to claim 1, wherein $R_1$, $R_2$ and $R_3$ are each independently a linear or branched aliphatic group having 1 to 4 carbon atoms.

4. The process according to claim 1, wherein the hydrogenation catalyst comprises 1 to 80% by weight of copper oxide.

5. The process according to claim 1, wherein the oxidic support of the hydrogenation catalyst comprises at least one oxide selected from the group consisting of aluminum oxides, silicon dioxide, titanium dioxides, zirconium dioxide, lanthanum oxide, molybdenum oxide, and tungsten oxide.

6. The process according to claim 1, wherein the hydrogenation catalyst does not comprise tungsten, molybdenum or oxides thereof.

7. The process according to claim 1, wherein the oxidic catalyst support is aluminum oxide and/or lanthanum oxide.

8. The process according to claim 1, wherein the molar ratio of alcohol II to primary amine III is 1.5 to 15:1.

9. The process according to claim 1, further comprising:
(a) distillatively removing alcohol II, optionally amine of the formula III and a portion of water from the reaction mixture comprising the secondary amine of formula I to obtain a reaction mixture residue,
(b) extracting the reaction mixture residue with an aqueous alkali metal and/or alkaline earth metal hydroxide solution to obtain a two phase aqueous/organic mixture,
(c) removing the aqueous phase of the two phase mixture from the organic phase,
(d) fractionally distilling the organic phase obtained from c) to obtain the secondary amine I and
(e) optionally, recycling water-comprising alcohol II and/or amine of the formula III into hydrogenation step (ii).

10. The process according to claim 1, wherein
the alcohol of formula II is ethanol,
the amine of formula III is tert-butylamine, and
the secondary amine of formula I is N-ethyl-tert-butylamine.

11. The process according to claim 1, wherein a solvent is added and the solvent is selected from the group of solvents selected from N-methylpyrrolidone, tetrahydrofuran, dioxane, ethylene glycol dimethyl ether, toluene, o-xylene, m-xylene and p-xylene.

12. The process according to claim 1, wherein the process is conducted in a cycle gas mode and hydrogen not reacted is recycled into the amination reaction.

13. The process according to claim 1, wherein the amine of formula II is adamantylamine.

14. The process according to claim 1, wherein the amine of formula II is cyclohexyl amine.

15. The process according to claim 1, wherein the alcohol of formula III comprises a primary alcohol which is selected from the group of primary alcohols consisting of methanol, ethanol, n-propanol, n-butanol, 2-methyl-1-propanol, pivalyl alcohol, n-pentanol, n-hexanol, 2-ethylhexanol, 2-methyl-1-pentanol, 3-methyl-1-pentanol, 4-methyl-1-pentanol, n-octanol, n-decanol, n-undecanol, n-dodecanol, 2-phenylethanol, 2-cyclopentylethanol, 2-cyclohexylethanol, 2-cycloheptylethanol, methylphenylethanol, benzyl alcohol and methylbenzyl alcohol.

16. The process according to claim 1, wherein the alcohol of formula III comprises a secondary alcohol which is selected from the group of secondary alcohols consisting of isopropyl alcohol, 2-butanol, cyclopentanol and cyclohexanol.

* * * * *